United States Patent

Fukada et al.

[11] 3,968,790
[45] July 13, 1976

[54] ELECTRET METHOD OF PROMOTING CALLUS FORMATION IN REGENERATION OF BONES

[75] Inventors: Eiichi Fukada, Wako; Toshiaki Takamatsu, Tokyo; Iwao Yasuda, Uji, all of Japan

[73] Assignee: Rikagaku Kenkyusho, Wako, Japan

[22] Filed: Feb. 26, 1975

[21] Appl. No.: 553,097

[52] U.S. Cl. .............................. 128/82.1; 128/92 G; 128/419 F; 3/1.9; 307/88 ET
[51] Int. Cl.² ...................... A61N 1/00; A61B 17/18
[58] Field of Search .............. 128/92 G, 92 D, 82.1, 128/419 F; 3/1, 1.9; 307/88 ET

[56] References Cited
UNITED STATES PATENTS

| | | | |
|---|---|---|---|
| 2,986,524 | 5/1961 | Padgett | 307/88 ET |
| 3,276,031 | 9/1966 | Gaynor | 307/88 ET |
| 3,449,094 | 6/1969 | Baxt et al. | 307/88 ET |
| 3,458,713 | 7/1969 | Perlman et al. | 307/88 ET |
| 3,706,131 | 12/1972 | Turnhout | 307/88 ET |
| 3,745,995 | 7/1973 | Kraus | 128/82.1 |

*Primary Examiner*—Ronald L. Frinks

[57] ABSTRACT

Disclosed is an electret for use in regeneration of bones which is essentially made of polytetrafluoroethylene (Teflon), polyhexafluoropropylene (FEP Teflon), polyester (Mylar), polypropylene and other substances having high molecular weight, or carnauba wax, bees wax, rosin and other waxy or resinous substances having lower molecular weight. The electret according to this invention when applied to broken bones will expedite the callus formation on bones.

5 Claims, 3 Drawing Figures

GROUP "A"

ELECTRET

GROUP "B"

ELECTRET

ELECTRET METHOD OF PROMOTING CALLUS FORMATION IN REGENERATION OF BONES

This invention relates to an electret for use in regeneration of bones.

The regeneration of bones is a characteristic of broken bones and ossifying myositis. It is known that if a spring is embedded in the marrow of a bone of a rabbit so as to subject the bone to stress, a regeneration of bone in the form of a spindle around the so-stressed bone results. This is called "non-fracture type callus formation." This sort of callus formation is also found if a bone is subjected to continuous mechanical vibration or heat generated by microwave energy. From these facts it appears that if an appreciable amount of energy is supplied to a bone, a regeneration of the bone results. Also, a piezoelectric phenomenon appears in regeneration of bones, and therefore it appears that energy in the form of electricity is useful in regeneration of bones. Callus formation on bones, in fact, results if the bone is subjected to an electrical stimulation via the musculature of a living body by using a microbattery and associated resistors.

The inventors in the present invention made numerous electrets from polytetrafluoroethylene (Teflon), polyhexafluoropropylene (FEP Teflon), polyester (Mylar), polypropylene and other substances having high molecular weight, or carnauba wax, bees wax, rosin and other waxy or resinous substances having lower molecular weight, and they found that if these electrets are embedded in a living body, a remarkable callus formation results. This invention was made on the basis of this discovery.

In this connection, one object of this invention is to provide an electret for callus formation on bone.

Another object of this invention is to provide a method of making such an electret.

To attain these objects an electret for callus formation on bone according to this invention comprises a dielectric body of a substance having low or high molecular weight with separate electric poles of opposite sign or one electric pole of a given sign and a stable existence that is to say, the dielectric body may bear a positive charge on one surface and a negative charge on the other; or it may have a positive or negative charge within the body of the electret. In any case the charge should remain in a stable state.

This invention will be better understood from the following description which is made with reference to the drawings.

EXAMPLE 1

Figure 1:
FIG. 1 shows the manner in which electrets are applied to bones.

A piece of Teflon film (25 $\mu$m thick) having aluminum plated on one surface of the film and an electric pole of a negative sign on the other surface of the film was used. Also, another piece of Teflon film (25 $\mu$m thick) having no plated aluminum and separate poles of opposite signs on both surfaces of the film. These first and second pieces of films were as large as $5 \times 5$ cm$^2$. Each of these films was put on a sheet of aluminium, and a point electrode was put 10 to 15 mm above the film. A dc voltage of 6 to 9 kilovolts was applied across the gap between the point electrode and the aluminum sheet electrode to produce a corona discharge at a room temperature for about 30 seconds. The density of electric charges on the surface of the film was 60 to 80 e.s.u./cm$^2$. Each of the so-charged films was cut and separated. Separate pieces of film ($20 \times 4$ mm$^2$) were used for callus formation. A film strip was attached to each thigh of a rabbit by cutting the skin and exposing the thigh bone from the musculature. Some of these film strips were attached in such a way as shown in the left part of FIG. 1, and the rest were attached in a way as shown in the right part of FIG. 1. The former is referred to as "Group A," and the latter is referred to as "Group B," hereinafter.

The result of Group A is given in Table 1.

Table 1

| Identification No. of Rabbits | | I | | II | | III |
|---|---|---|---|---|---|---|
| Thigh (L: left; R: right) | | L | R | L | R | L | R |
| Amount of Electric Charge on Teflon | | 0 | | 60 – 80 e.s.u./cm$^2$ | | |
| Sign of Electric Charge on the Surface of Teflon facing the Bone | | 0$^{nl}$ | (−)$^{nl}$ | (−) | (+) | (−) | (+) |
| Extent of Callus Formation in X-ray Photos* | in a week | − | − | − | − | ± | − |
| | in 2 weeks | − | ± | + | + | + | + |
| | in 3 weeks | − | + | ++ | + | + | + |
| | in 4 weeks | − | + | ++ | + | ++ | + |

\*indicates no callus formation;
± indicates some callus formation and
+ indicates substantial callus formation.;

As shown in the table, particularly I-L, aluminum-coated film strips bearing no electric charges were used, and X-ray photos showed no callus formation even after the lapse of four weeks.

As shown in the column I-R of the table, X-ray photos showed after the elapse of one week, no callus formation on the bones to which the aluminum-coated film strips bearing minus electric charge on the surface opposite to the plated surface of the film strips. However, X-ray photos revealed that callus was formed on the bone in two weeks.

Figure 2:
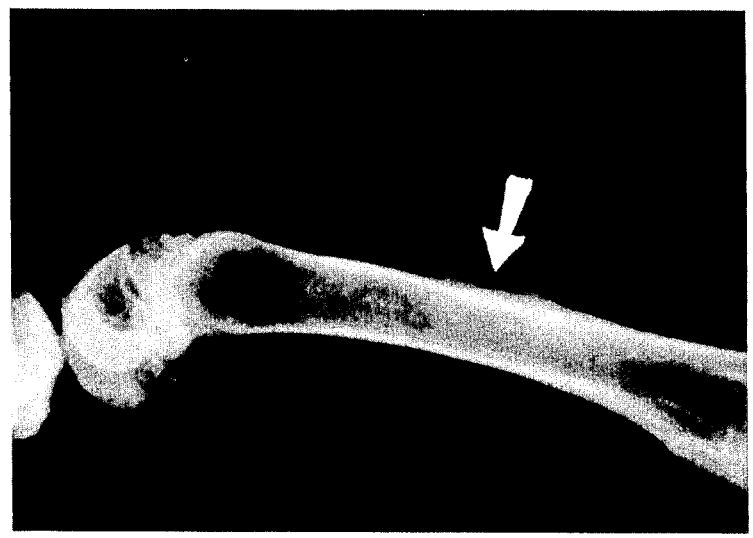
FIGS. 2 and 3 are X-ray photographs showing callus formation on the bones to which electrets were applied according to this invention.

The column II-L of the table pertains to electrets having no aluminum coating and bearing minus electric charge on the film surface against the bone and plus electric charge on the other film surface, and the table shows the callus formation after the lapse of two weeks. Similar electrets bearing electric charges of opposite sign in the opposite way to II-L electrets were used, and similar results were attained. FIG. 2 shows an X-ray image of the callus formation on bone after the lapse of two weeks.

From the experimental data of Group A it is established that:

1. Teflon films bearing no electric charge, whether plated or not, are useless in forming a discernible amount of callus on bone within 4 weeks;
2. Teflon film electrets are useful in expediting callus formation on bone. X-ray photos show the callus formation after the lapse of two weeks; and
3. Whichever charged side of the electret may be put on the bone, a callus formation results.

The results of Group B is given in Table II.

Table II

| Identification No. of Rabbits | I | | II | |
|---|---|---|---|---|
| Thigh (L: Left; R: Right) | L | R | L | R |
| Amount of Electric Charge on Teflon | 60 – 80 e.s.u./cm² | | | |
| X-ray Images of Callus Formation | ++ | ++ | +++ | ++ |

Group B is composed of non-plated Teflon films which were attached to the bones to encircle them with a view to subjecting the whole annular area of the bone to electric stress. Care should be taken not to injure the periosteum of the bone, and therefore the electret was loosely attached to the bone so that the bone may not be subjected to a mechanical stress.

Figure 3:
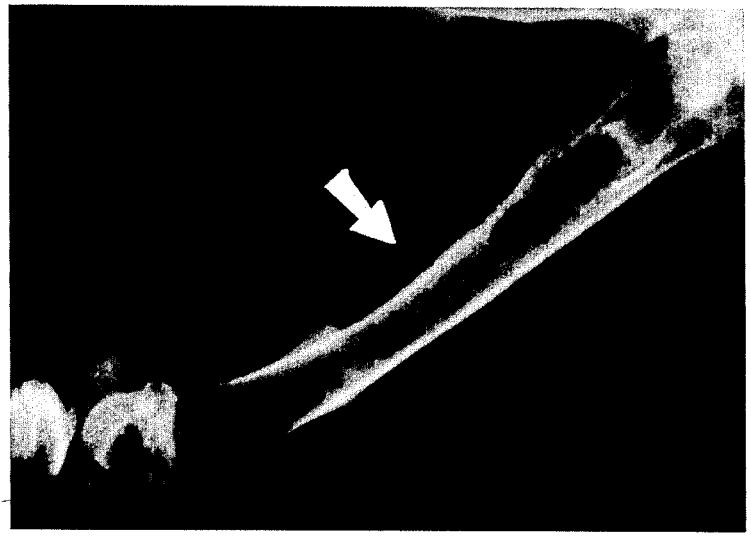

Columns I-L, I-R, II-L and II-R of the table show remarkable callus formation. FIG. 3 shows an X-ray image of callus formation on the bone after the lapse of 2 weeks.

EXAMPLE 2

Electrets were made of waxy or resinous substances having a lower molecular weight as follows:

A proper amount of carnauba wax was mixed with bees wax or rosin, and the mixture was heated. This material was allowed to drop and flow on hot stainless steel plates (5 × 5 × 0.01 to 0.05 cm²) at 100°C, and coating films 0.1 to 0.3 mm thick resulted when cold. A point electrode was put 10 mm above the wax or resin film, and a voltage of 6 kilovolts was applied to the space between the underlying plate and the point electrode, thus subjecting the wax or resin film to corona discharge. The density of electric charge on the film surface was 50 to 100 e.s.u./cm². Alternatively, an aluminum foil was put on the film, and a dc voltage almost equal to the breakdown voltage at a temperature as high as the melting point, and then the so treated film was allowed to grow cold to the room temperature. Thus, the electret resulted, and the electric charge was retained for an extended length of time.

The so-produced electrets were applied to the thighs of rabbits, and the callus formation was observed after the lapse of 2 weeks.

As seen from the above examples, if an electret of a substance having a high or low molecular weight is applied to the bone, a callus formation thereon is substantially expedited, and such an electret has anti-thrombogenicity and therefore it is advantageous to curing broken bones.

The examples given above should not be understood as limitative, but electrets of different materials and sizes other than those given above may be used, and preferably the density of electric charge is above 30 e.s.u./cm².

What is claimed is:

1. A method of promoting callus formation on bones comprising applying to a bone an electret composed of a material selected from the group consisting of polytetrafluoroethylene, polyhexafluoropryopylene, polyesters, polypropylene, carnauba wax, bees wax, and rosin, said electret being charged, prior to application to the bone, at a density of at least 30 e.s.u./cm².

2. A method according to claim 1 wherein the electret is charged at a density of from about 60 to 80 e.s.u./cm².

3. A method according to claim 2, wherein said electret is affixed to a surface of the bone.

4. A method according to claim 2, wherein said electret is implanted to substantially surround the bone.

5. A method according to claim 1, wherein said electret material is in the form of a film having a metallic coating thereon.

* * * * *